United States Patent [19]

Becker et al.

[11] Patent Number: 4,975,453

[45] Date of Patent: Dec. 4, 1990

[54] COMBINATION OF ANGIOTENSIN CONVERTING ENZYME INHIBITORS WITH POTASSIUM CHANNEL MODULATORS AND USE THEREOF IN PHARMACEUTICALS

[75] Inventors: Reinhard Becker, Wiesbaden; Rainer Henning, Hattersheim am Main; Hansjörg Urbach, Kronberg/Taunus; Volker Teetz; Heinrich C. Englert, both of Hofheim am Taunus; Dieter Mania, Kelkheim, all of Fed. Rep. of Germany

[73] Assignee: Hoechst Aktiengesellschaft, Frankfurt am Main, Fed. Rep. of Germany

[21] Appl. No.: 357,822

[22] Filed: May 26, 1989

[30] Foreign Application Priority Data

May 28, 1988 [DE] Fed. Rep. of Germany ....... 3818245

[51] Int. Cl.$^5$ ..................... A01N 43/16; A61K 31/35

[52] U.S. Cl. .................................. 514/456; 548/452; 549/398

[58] Field of Search ................ 548/525; 514/449, 422, 514/430

[56] References Cited

FOREIGN PATENT DOCUMENTS 271271 6/1988 European Pat. Off. ......... 514/235.8

*Primary Examiner*—Mukund J. Shah
*Assistant Examiner*—Deborah D. Carr
*Attorney, Agent, or Firm*—Finnegan, Henderson, Farabow, Garrett, and Dunner

[57] ABSTRACT

Combination of angiotensin converting enzyme inhibitors with potassium channel modulators and use thereof in pharmaceuticals.

The invention relates to combinations of angiotensin converting enzyme inhibitors with potassium channel modulators, processes for their preparation and use thereof as medicaments.

17 Claims, No Drawings

COMBINATION OF ANGIOTENSIN CONVERTING ENZYME INHIBITORS WITH POTASSIUM CHANNEL MODULATORS AND USE THEREOF IN PHARMACEUTICALS

DESCRIPTION

The present invention relates to a combination of angiotensin converting enzyme inhibitors (ACE inhibitors) with potassium channel modulators and use thereof in pharmaceuticals, in particular in hypotensive pharmaceuticals.

ACE inhibitors are compounds which prevent the conversion of angiotensin I into the pressor-active angiotensin II. Such compounds are described, for example, in the following patent applications or patents: U.S. Pat. Nos. 4,350,633, 4,344,949, 4,294,832, 4,350,704, EP-A Nos. 50,800, 31,741, 51,020, 49,658, 49,605, 29,488, 46,953, 52,870, 72,022, 84,164, 89,637, 90,341, 90,362, 105,102, 109,020, 111,873, 113,880.

Their hypotensive action is well documented. Potassium channel modulators are those compounds which influence the outflow of potassium ions from cells, in particular smooth muscle cells, and thereby lead to a membrane hyperpolarization. Such compounds and their hypotensive action are set down in patent applications and publications, for example in J. Med. Chem. 29 (1986) 2194-2201 and European Patent Applications EP-A No. 76,075, 107,423, 120,427 and 120,428.

Both groups of substances intervene in various blood pressure regulation systems. Surprisingly here, on combined administration the effect of the one component of the combination is increased by the other respective component. On combined administration, this leads to a lowering of the dose of the respective components of the combination, compared with individual administration. In this way, the occurrence of side effects known for the two classes of substances can be lowered or avoided. Combinations of representatives of these classes of active compound have not previously been described.

Suitable ACE inhibitors are the following compounds of the formula I or their physiologically tolerable salts:

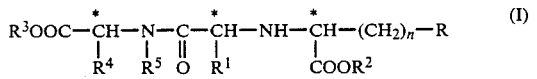

in which n is 1 or 2,

R denotes hydrogen,
an optionally substituted aliphatic radical having 1-8 carbon atoms,
an optionally substituted alicyclic radical having 3-9 carbon atoms,
an optionally substituted aromatic radical having 6-12 carbon atoms,
an optionally substituted araliphatic radical having 7-14 carbon atoms,
an optionally substituted alicyclic-aliphatic radical having 7-14 carbon atoms,
a radical $OR^a$ or $SR^a$, in which
$R^a$ represents an optionally substituted aliphatic radical having 1-4 carbon atoms, an optionally substituted aromatic radical having 6-12 carbon atoms or an optionally substituted heteroaromatic radical having 5-12 ring atoms, $R^1$ denotes hydrogen,
an optionally substituted aliphatic radical having 1-6 carbon atoms,
an optionally substituted alicyclic radical having 3-9 carbon atoms,
an optionally substituted alicyclic-aliphatic radical having 4-13 carbon atoms,
an optionally substituted aromatic radical having 6-12 carbon atoms,
a optionally substituted araliphatic radical having 7-16 carbon atoms,
an optionally substituted heteroaromatic radical having 5-12 ring atoms or
the side chain, protected if necessary, of a naturally occurring α-amino acid, $R^2$ and $R^3$ are identical or different and denote hydrogen,
an optionally substituted aliphatic radical having 1-6 carbon atoms,
an optionally substituted alicyclic radical having 3-9 carbon atoms,
an optionally substituted aromatic radical having 6-12 carbon atoms,
an optionally substituted araliphatic radical having 7-16 carbon atoms and $R^4$ and $R^5$ together with the atoms carrying them form a heterocyclic bi- or tricyclic ring system having 5 to 15 carbon atoms.

Suitable ring systems of this type are in particular those from the following group: tetrahydroisoquinoline (A); decahydroisoquinoline (B); octahydroindole (C); octahydrocyclopenta[b]pyrrole (D); 2-azaspiro[4.5]decane (E); 2-azaspiro[4.4]nonane (F); spiro[(bicyclo[2.2.1]heptane)-2,3'-pyrrolidine] (G); spiro[(bicyclo[2.2.2]octane)-2,3'-pyrrolidine] (H); 2=azatricyclo[4.3.0.1^{6,9}]-decane (I); decahydrocyclohepta[b]pyrrole (J); octahydroisoindole (K); octahydrocyclopenta[c]pyrrole (L); 2,3,3a,4,5,7a-hexahydroindole (M); 2-azabicyclo[3.1.0]hexane (N); hexahydrocyclopenta[b]pyrrole (O), which can all be optionally substituted. However, the unsubstituted systems are preferred.

In the compounds which have a number of chiral atoms, suitable racemates or enantiomers are all possible diastereomers, or mixtures of different diastereomers.

The cyclic amino acid esters which are suitable have the following structural formulae.

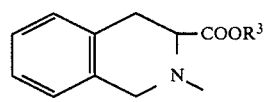 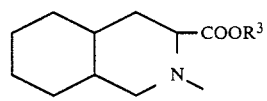

A            B

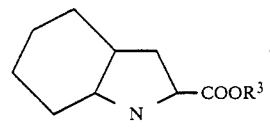 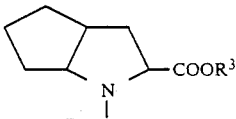

C            D

-continued

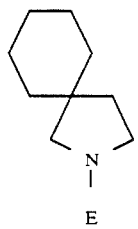
E

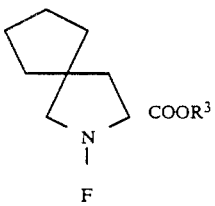
F

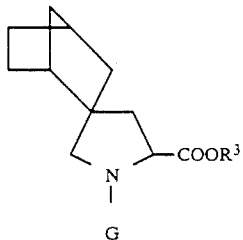
G

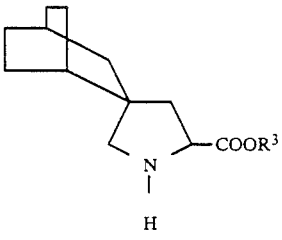
H

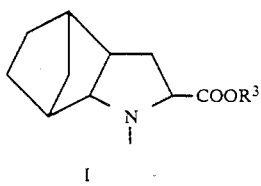
I

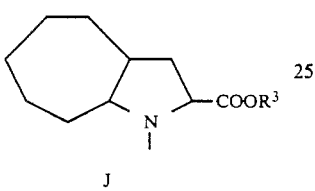
J

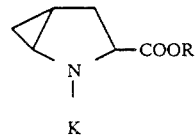
K

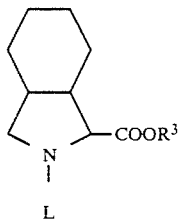
L

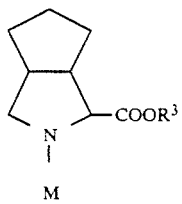
M

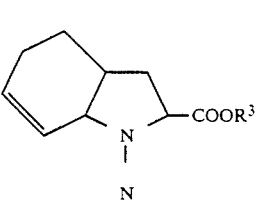
N

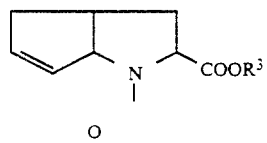
O

Particularly preferred ACE inhibitors are those of the formula I in which
n is 1 or 2
R denotes hydrogen,
 alkyl having 1–8 carbon atoms,
 alkenyl having 2–6 carbon atoms,
 cycloalkyl having 3–9 carbon atoms,
 aryl having 6–12 carbon atoms,
  which can be monosubstituted, disubstituted or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-alkanoylamino, methylenedioxy, cyano and/or sulfamoyl,
 alkoxy having 1–4 carbon atoms,
 aryloxy having 6–12 carbon atoms,
  which can be substituted as described above for aryl,
 mono- or bicyclic heteroaryloxy having 5–7 or 8–10 ring atoms, of which 1 or 2 ring atoms are sulfur or oxygen atoms and/or 1 to 4 ring atoms are nitrogen,
  which can be substituted as described above for aryl,
 amino-$(C_1-C_4)$-alkyl,
 $(C_1-C_4)$-alkanoylamino-$(C_1-C_4)$-alkyl,
 $(C_7-C_{13})$-aroylamino-$(C_1-C_4)$-alkyl,
 $(C_1-C_4)$-alkoxycarbonylamino-$(C_1-C_4)$-alkyl,
 $(C_6-C_{12})$-aryl-$(C_1-C_4)$-alkoxycarbonylamino-$(C_1-C_4)$-alkyl,
 $(C_6-C_{12})$-aryl-$(C_1-C_4)$-alkylamino-$(C_1-C_4)$-alkyl,
 $(C_1-C_4)$-alkylamino-$(C_1-C_4)$-alkyl,
 di-$(C_1-C_4)$-alkylamino-$(C_1-C_4)$-alkyl,
 guanidino-$(C_1-C_4)$-alkyl,
 imidazolyl, indolyl,
 $(C_1-C_4)$-alkylthio,
 $(C_1-C_4)$-alkylthio-$(C_1-C_4)$-alkyl,
 $(C_6-C_{12})$-arylthio-$(C_1-C_4)$-alkyl,
  which can be substituted in the aryl moiety as described above for aryl,
 $(C_6-C_{12})$-aryl-$(C_1-C_4)$-alkylthio,
  which can be substituted in the aryl moiety as described above for aryl,
 carboxyl-$(C_1-C_4)$-alkyl,
 carboxyl, carbamoyl,
 carbamoyl-$(C_1-C_4)$-alkyl,
 $(C_1-C_4)$-alkoxycarbonyl-$(C_1-C_4)$-alkyl,
 $(C_6-C_{12})$-aryloxy-$(C_1-C_4)$-alkyl,
  which can be substituted in the aryl moiety as described above for aryl or
 $(C_6-C_{12})$-aryl-$(C_1-C_4)$-alkoxy,
  which can be substituted in the aryl moiety as described above for aryl,
$R^1$ denotes hydrogen,
 alkyl having 1–6 carbon atoms,
 alkenyl having 2–6 carbon atoms,
 alkynyl having 2–6 carbon atoms,
 cycloalkyl having 3–9 carbon atoms,
 cycloalkenyl having 5–9 carbon atoms,
 $(C_3-C_9)$-cycloalkyl-$(C_1-C_4)$-alkyl,
 $(C_5-C_9)$-cycloalkenyl-$(C_1-C_4)$-alkyl, aryl, which is optionally partly hydrogenated, having 6–12 carbon atoms, which can be substituted as described above for R,
 $(C_6-C_{12})$-aryl-$(C_1-C_4)$-alkyl or $(C_7-C_{13})$-aroyl-$(C_1$ or $C_2)$-alkyl
  which can both be substituted like the above mentioned aryl,
 mono- or bicyclic heteroaryl, which is optionally partly hydrogenated, having 5–7 or 8–10 ring atoms, of which 1 or 2 ring atoms are sulfur or oxygen atoms and/or 1 to 4 ring atoms are nitrogen atoms,
  which can be substituted like the abovementioned aryl or the optionally protected side chain of a naturally occurring α-amino acid $R^1$—CH(NH$_2$)—COOH,
$R^2$ and $R^3$ are identical or different and denote hydrogen,
 alkyl having 1–6 carbon atoms, alkenyl having 2-6 carbon atoms,
di-($C_1$-$C_4$)-alkylamino-($C_1$-$C_4$)-alkyl,
($C_1$-$C_5$)-alkanoyloxy-($C_1$-$C_4$)-alkyl,
($C_1$-$C_6$)-alkoxycarbonyloxy-($C_1$-$C_4$)-alkyl,
($C_7$-$C_{13}$)-aroyloxy-($C_1$-$C_4$)-alkyl,
($C_6$-$C_{12}$)-aryloxycarbonyloxy-($C_1$-$C_4$)-alkyl, aryl having 6-12 carbon atoms,
($C_6$-$C_{12}$)-aryl-($C_1$-$C_4$)-alkyl,
($C_3$-$C_9$)-cycloalkyl or
($C_3$-$C_9$)-cycloalkyl-($C_1$-$C_4$)-alkyl and
$R^4$ and $R^5$ have the abovementioned meaning.

Particularly preferred compounds of the formula I are those in which
n is 1 or 2,
R denotes ($C_1$-$C_6$)-alkyl, ($C_2$-$C_6$)-alkenyl, ($C_3$-$C_9$)-cycloalkyl, amino-($C_1$-$C_4$)-alkyl, ($C_2$-$C_5$)-acylamino-($C_1$-$C_4$)-alkyl, ($C_7$-$C_{13}$)-aroylamino-($C_1$-$C_4$)-alkyl, ($C_1$-$C_4$)-alkoxycarbonylamino-($C_1$-$C_4$)-alkyl, ($C_6$-$C_{12}$)-aryl-($C_1$-$C_4$)-alkoxycarbonylamino-($C_1$-$C_4$)-alkyl, ($C_6$-$C_{12}$)-aryl which can be monosubstituted, disubstituted or trisubstituted by ($C_1$-$C_4$)-alkyl, ($C_1$-$C_4$)-alkoxy, hydroxyl, halogen, nitro, amino, ($C_1$-$C_4$)-alkylamino, di-($C_1$-$C_4$)-alkylamino and/or methylenedioxy, or 3-indolyl, in particular methyl, ethyl, cyclohexyl, tert.-butoxycarbonylamino-($C_1$-$C_4$)-alkyl, benzoyloxycarbonylamino-($C_1$-$C_4$)-alkyl or phenyl which can be monosubstituted or disubstituted by phenyl, ($C_1$-$C_2$)-alkyl, ($C_1$ or $C_2$)-alkoxy, hydroxyl, fluorine, chlorine, bromine, amino, ($C_1$-$C_4$)-alkylamino, di-($C_1$-$C_4$)-alkylamino, nitro and/or methylenedioxy or, in the case of methoxy, trisubstituted, $R^1$ denotes hydrogen or ($C_1$-$C_6$)-alkyl which can optionally be substituted by amino, ($C_1$-$C_6$)-acylamino or benzoylamino, ($C_2$-$C_6$)-alkenyl, ($C_3$-$C_9$)-cycloalkyl, ($C_5$-$C_9$)-cycloalkenyl, ($C_3$-$C_7$)-cycloalkyl-($C_1$-$C_4$)-alkyl, ($C_6$-$C_{12}$)-aryl or partly hydrogenated aryl, which in each case can be substituted by ($C_1$-$C_4$)-alkyl, ($C_1$ or $C_2$)-alkoxy or halogen, ($C_6$-$C_{12}$)-aryl-($C_1$-$C_4$)-alkyl or ($C_7$-$C_{13}$)-aroyl-($C_1$-$C_2$)-alkyl, which can both be substituted in the aryl radical as defined in the foregoing, a mono- or bicyclic heterocyclic radical having 5 to 7 or 8 to 10 ring atoms, of which 1 or 2 ring atoms are sulfur or oxygen atoms and/or 1 to 4 ring atoms are nitrogen atoms, or a side chain of a naturally occurring, optionally protected α-amino acid, but in particular hydrogen, ($C_1$-$C_3$)-alkyl, ($C_2$ or $C_3$)-alkenyl, the optionally protected side chain of lysine, benzyl, 4-methoxybenzyl, 4-ethoxybenzyl, phenethyl, 4-aminobutyl or benzoylmethyl, $R^2$ and $R^3$ denote identical or different radicals, hydrogen, ($C_1$-$C_6$)-alkyl, ($C_2$-$C_6$)-alkenyl or ($C_6$-$C_{12}$)-aryl-($C_1$-$C_4$)-alkyl, but in particular hydrogen, ($C_1$-$C_4$)-alkyl or benzyl and
$R^4$ and $R^5$ have the abovementioned meaning.

Aryl, here as in the following, is preferably to be understood as meaning optionally substituted phenyl, biphenylyl or naphthyl. The same applies to radicals derived from aryl such as aryloxy or arylthio. Aroyl is to be taken as meaning, in particular, benzoyl. Aliphatic radicals can be straight-chain or branched.

A mono- or bicyclic heterocyclic radical having 5 to 7 or 8 to 10 ring atoms, of which 1 or 2 ring atoms are sulfur or oxygen atoms and/or of which 1 to 4 ring atoms are nitrogen atoms is to be taken as meaning, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated.

Naturally occurring α-amino acids are, for example, described in Houben-Weyl, Methoden der Organischen Chemie (Methods of Organic Chemistry), Vol. XV/1 and XV/2.

If $R^1$ represents a side chain of a protected naturally occurring α-amino acid, such as, for example, protected Ser, Thr, Asp, Asn, Glu, Gln, Arg, Lys, Hyl, Cys, Orn, Cit, Tyr, Trp, His or Hyp, groups which are customary in peptide chemistry as protective groups are preferred (compare Houben-Weyl, Vol. XV/1 and XV/2). In the case in which $R^1$ denotes the protected lysine side chain, the known amino protective groups, but in particular Z, Boc or ($C_1$-$C_6$)-alkanoyl, are preferred. Possible O-protective groups for tyrosine are preferably ($C_1$-$C_6$)-alkyl, in particular methyl or ethyl.

Particularly preferred compounds are 2-[N-(1-S-ethoxycarbonyl-3-phenylpropyl)-S-alanyl]-(1S,3S,5S)-2-azabicyclo[3.3.0]octane-3-carboxylic acid (ramipril), 1-[N-(1-S-ethoxycarbonyl-3-phenylpropyl)-S-alanyl]-(2S,3aR,7aS)-octahydro[1H]indole-2-carboxylic acid (trandolapril) and 2-[N-(1-S-ethoxycarbonyl-3-phenylpropyl)-S-alanyl]-1,2,3,4-tetrahydroisoquinoline-3-S-carboxylic acid (quinapril).

The preparation of the ACE inhibitors of the formula I is described in the patent applications or patents mentioned on page 1.

Suitable potassium channel modulators are compounds of the formula II

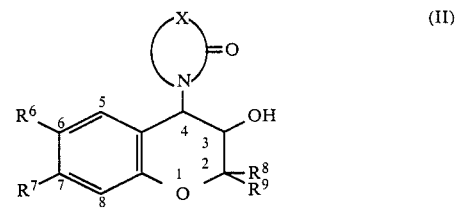

in which
$R^6$ represents CN, $NO_2$, $SO_n$—($C_1$-$C_6$)-alkyl or $SO_n$—Ar, where n is 1 or 2, Ar represents an aromatic or heteroaromatic system which is unsubstituted or substituted by 1 to 3 identical or different radicals from the series comprising ($C_1$-$C_2$)-alkyl, ($C_1$-$C_2$)-alkoxy, halogen, trifluoromethyl, CN, $NO_2$, CO-($C_1$-$C_2$)-alkyl or $SO_p$—($C_1$-$C_2$)-alkyl and p represents 1 or 2,
$R^7$ represents hydrogen, hydroxyl, ($C_1$-$C_2$)-alkoxy, ($C_1$-$C_2$)-alkyl, halogen or $NR^{10}R^{11}$, where $R^{10}$ and $R^{11}$ are identical or different and represent hydrogen, ($C_1$-$C_2$)-alkyl or ($C_1$-$C_2$)-alkylcarbonyl, where the abovementioned meanings of $R^6$ and $R^7$ can also be interchanged,
$R^8$ and $R^9$ are identical or different and represent alkyl having 1-4 carbon atoms,
X represents a $(CH_2)_m$ chain which is unsubstituted or substituted by at least 1 and at most $2m-1$ ($C_1$-$C_2$)-alkyl groups, and can be interrupted by a heteroatom Y with the meaning of O, $NR^{12}$ or S and $R^{12}$ denotes H or ($C_1$-$C_4$)-alkyl and m represents 2, 3 or 4, where the configuration of $C_3$ and $C_4$ is always opposite.

An aromatic system Ar is preferably understood as meaning phenyl, naphthyl or biphenylyl, a 5 or 6-membered heteroaromatic system Ar is preferably a radical of a 5 or 6-membered O, N and/or S heterocyclic ring, in particular furyl, thienyl, isothiazolyl, oxazolyl, isoxazolyl, pyrazolyl, imidazolyl, thiazolyl, pyridyl, pyrazinyl, pyrimidinyl, pyridazinyl or thiazinyl.

Halogen is understood as meaning F, Cl, Br or I, preferably F and Cl.

The carbon atoms 3 and 4 of the 3,4-dihydro-2H-benzo[b]pyran system (subsequently also designated as "chroman system") of the formula II are asymmetrically substituted. The invention relates only to those compounds which have opposite configurations at these centers. This means that the lactam ring as a substituent on C-4 and the OH group on C-3 are always orientated "trans" to one another. The abovementioned definition of X means that in addition the lactam ring contains at least one, but at most m (m having the definition mentioned at the beginning), chiral carbon atoms. The invention thus relates both to compounds having centers both with the R- and the S-configuration. The same applies in the case in which $R^6$, $R^7$, $R^8$ and $R^9$ contain centers of asymmetry or produce a center of symmetry with themselves as substituents. The compounds can then exist as optical isomers, as diastereomers, as racemates or as a mixture thereof.

Preferred compounds are those of the formula II in which $R^6$, $R^7$, $R^8$ and $R^9$ have the abovementioned meanings and X represents a $(CH_2)_m$ chain which is unsubstituted or substituted by a $(C_1-C_2)$-alkyl group, and can be interrupted by a heteroatom Y which represents O, S or $NR^{12}$ with $R^{12}$ having the meaning of hydrogen or $(C_2-C_4)$-alkyl, and where m represents 2, 3 or 4.

Further preferred compounds of the formula II are those in which $R^6$ to $R^9$ have the abovementioned meanings and x represents a $(CH_2)_m$ chain which is unsubstituted or substituted by a $(C_1-C_2)$-alkyl group where m represents 3 or 4.

Very particularly preferred compounds here are those of the formula II in which $R^6$ to $R^9$ have the abovementioned meanings and X represents a $(CH_2)_m$ chain, where m represents 3 or 4, which is substituted by a $(C_1-C_2)$-alkyl group on the carbon atom which is adjacent to the nitrogen atom of the lactam ring.

Particularly preferred compounds are those in which $R^6$ to $R^9$ have the abovementioned meanings and X represents a $(CH_2)_m$ chain having m=3 or 4 which is unsubstituted or substituted by a $(C_1-C_2)$-alkyl group on the carbon atom which is adjacent to the nitrogen atom of the lactam ring, in particular in such a way that the configuration of this carbon atom is the same as that of the 4-carbon atom of the chroman system.

Very particularly preferred compounds are also those of the formula II in which $R^6$ represents CN or $SO_2$—$CH_3$ and $R^7$ represents hydrogen, $R^8$ and $R^9$ are identical or different and represent alkyl having 1 or 2 carbon atoms, X represents a $(CH_2)_m$ chain having m=3 or 4 which is unsubstituted or substituted by a $(C_1-C_2)$-alkyl group on the carbon atom which is adjacent to the nitrogen atom of the lactam ring, in particular in such a way that the configuration of this carbon atom is the same as that of the 4-carbon atom in the chroman system;

similarly preferred compounds are those compounds II in which $R^6$ represents $SO_2$—Ar with Ar having the meaning of phenyl which is unsubstituted or substituted by 1 to 3 substituents as mentioned above, $R^7$ represents hydrogen or $OCH_3$, $R^8$ and $R^9$ are identical or different and represent $(C_1-C_2)$-alkyl, X represents a $(CH_2)_m$ chain having m=3 or 4 which is unsubstituted or substituted by a $(C_1-C_2)$-alkyl group on the carbon atom which is adjacent to the- nitrogen atom of the lactam ring, in particular in such a way that the configuration of this carbon atom is the same as that of the 4-carbon atom in the chroman system.

Preferred compounds are also those in which $R^6$ to $R^9$ have the abovementioned meanings and X represents a $(CH_2)_m$ chain having M=3 or 4 which is unsubstituted or substituted by a $(C_1-C_2)$-alkyl group on the carbon atom which is adjacent to the nitrogen atom of the lactam ring, in particular in such a way that the configuration of this carbon atom is opposite to that of the 4-carbon atom of the chroman system.

Very particularly preferred compounds II are also those in which $R^6$ represents CN or $SO_2$—$CH_3$ and $R^7$ represents hydrogen, $R^8$ and $R^9$ are identical or different and represent alkyl having 1 or 2 carbon atoms, X represents a $(CH_2)_m$ chain having m=3 or 4 which is unsubstituted or substituted by a $(C_1-C_2)$-alkyl group on the carbon atom which is adjacent to the nitrogen atom of the lactam ring, in particular in such a way that the configuration of this carbon atom is opposite to that of the 4-carbon atom in the chroman system;

similarly preferred compounds are those compounds II in which $R^6$ represents $SO_2$—Ar with Ar having the meaning of phenyl which is unsubstituted or substituted by 1 to 3 substituents as mentioned above, $R^7$ represents hydrogen or $OCH_3$, $R^8$ and $R^9$ are identical or different and represent $(C_1-C_2)$-alkyl, X represents a $(CH_2)_m$ chain having m=3 or 4 which is unsubstituted or substituted by a $(C_1-C_2)$-alkyl group on the carbon atom which is adjacent to the nitrogen atom of the lactam ring, in particular in such a way that the configuration of this carbon atom is opposite to that of the 4-carbon atom in the chroman system.

The following combinations are of very particular significance:

ramipril+(±)-6-cyano-3,4-dihydro-2,2-dimethyl-trans-4-(2-oxo-1-pyrrolidinyl)-2H-benzo[b]pyran-3-ol (chromakalim), ramipril+6-cyano-3-hydroxy-2,2-dimethyl-4-(5-methyl-2-oxo-1-pyrrolidinyl)-3,4-dihydro-2H-benzo[b]pyran, ramipril+2,2-dimethyl-3-hydroxy-6-phenylsulfonyl-4-(2-oxo-1-pyrrolidinyl)-3,4-dihydro-2H-benzo[b]pyran, trandolapril+chromakalim, trandolapril+6-cyano-3-hydroxy-2,2-dimethyl-4-(5-methyl-2-oxo-1-pyrrolidinyl)-3,4-dihydro-2H-benzo[b]pyran, trandolapril+2,2-dimethyl-3-hydroxy-6-phenylsulfonyl-4-(2-oxo-1-pyrrolidinyl)-3,4-dihydro-2H-benzo[b]pyran, quinapril+chromakalim, quinapril+6-cyano-3-hydroxy-2,2-dimethyl-4-(5-methyl-2-oxo-1-pyrrolidinyl)-3,4-dihydro-2H-benzo[b]pyran, quinapril+2,2-dimethyl-3-hydroxy-6-phenylsulfonyl-4-(2-oxo-1-pyrrolidinyl)-3,4-dihydro-2H-benzo[b]pyran, ramipril+(3S,4R)-6-cyano-3,4-dihydro-2,2-dimethyl-4-(2-oxo-1-pyrrolidinyl)-2H-benzo[b]pyran-3-ol, trandolapril+(3S,4R)-6-cyano-3,4-dihydro-2,2-dimethyl-4-(2-oxo-1-pyrrolidinyl)-2H-benzo[b]pyran-3-ol, quinapril+(3S,4R)-6-cyano-3,4-dihydro-2,2-dimethyl-4-(2-oxo-1-pyrrolidinyl)-2H-benzo[b]pyran-3-ol, ramipril+(3S,4R)-6-phenylsulfonyl-3,4-dihydro-2,2-dimethyl-4-(2-oxo-1-pyrrolidinyl)-2H-benzo[b]pyran-3-ol, trandolapril+(3S,4R)-6-phenylsulfonyl-3,4-dihydro-2,2-dimethyl-4-(2-oxo-1-pyrrolidinyl)-2H-benzo[b]pyran-3-ol, quinapril+(3S,4R)-6-phenylsulfonyl-3,4-dihydro-2,2-dimethyl-4-(2-oxo-1-pyrrolidinyl)-2H-benzo[b]pyran-3-ol and in each case the physiologically tolerable salts of the individual components mentioned, if these can be formed.

Potassium channel modulators can be prepared by the process described in J. Med. Chem. 29 (1986) 2194–2201, EP-A Nos. 76,075, 107,423, 120,427 and 120,428.

The invention also relates to very general products which contain:
(a) an ACE inhibitor of the formula I or its physiologically tolerable salt and
(b) a potassium channel modulator of the formula II or its physiologically tolerable salt as a combination preparation for simultaneous, separate or sequential administration in the treatment of high blood pressure.

Table 1 shows the mean arterial blood pressure, measured on the conscious spontaneously hypertonic rat analogously to the method described in Arzneimittelforschung 34 (II), p. 1419 (1984).

TABLE 1

| t [min] | mean arterial pressure [mmHg] ± SEM (n = 6) Group | | | | | |
|---|---|---|---|---|---|---|
|  | 1 | 2 | 3 | 4 | 5 | 6 |
| 0   | 164 ± 8 | 136 ± 8  | 153 ± 8  | 162 ± 6  | 166 ± 6 | 154 ± 3 |
| 2   | 158 ± 4 | 167 ± 10 | 139 ± 16 | 152 ± 9  | 158 ± 6 | 155 ± 7 |
| 3   | 158 ± 4 | 162 ± 9  | 134 ± 16 | 124 ± 10 | 151 ± 5 | 143 ± 8 |
| 5   | 161 ± 8 | 165 ± 8  | 111 ± 12 | 107 ± 7  | 137 ± 4 | 120 ± 13 |
| 10  | 163 ± 8 | 151 ± 11 | 89 ± 9   | 84 ± 5   | 116 ± 6 | 91 ± 4 |
| 15  | 164 ± 8 | 141 ± 12 | 89 ± 8   | 84 ± 4   | 103 ± 6 | 86 ± 3 |
| 20  | 161 ± 8 | 139 ± 13 | 84 ± 7   | 79 ± 4   | 96 ± 7  | 82 ± 3 |
| 25  | 163 ± 8 | 138 ± 13 | 88 ± 7   | 78 ± 3   | 94 ± 9  | 79 ± 3 |
| 30  | 160 ± 8 | 142 ± 15 | 86 ± 6   | 82 ± 3   | 94 ± 8  | 83 ± 3 |
| 35  | 161 ± 8 | 139 ± 14 | 87 ± 5   | 82 ± 3   | 106 ± 5 | 86 ± 2 |
| 40  | 159 ± 7 | 139 ± 14 | 90 ± 4   | 82 ± 4   | 106 ± 5 | 88 ± 2 |
| 45  | 159 ± 7 | 141 ± 13 | 92 ± 4   | 82 ± 4   | 109 ± 5 | 87 ± 3 |
| 50  | 158 ± 9 | 142 ± 11 | 92 ± 4   | 84 ± 3   | 113 ± 4 | 91 ± 4 |
| 55  | 158 ± 9 | 143 ± 11 | 98 ± 5   | 85 ± 3   | 118 ± 3 | 93 ± 4 |
| 60  | 162 ± 8 | 143 ± 11 | 99 ± 4   | 87 ± 4   | 119 ± 3 | 95 ± 5 |
| 75  | 156 ± 9 | 144 ± 13 | 108 ± 7  | 87 ± 4   | 124 ± 4 | 98 ± 5 |
| 90  | 161 ± 6 | 142 ± 11 | 111 ± 8  | 90 ± 4   | 123 ± 4 | 96 ± 3 |
| 105 | 157 ± 6 | 139 ± 12 | 113 ± 7  | 92 ± 5   | 114 ± 6 | 92 ± 3 |
| 120 | 153 ± 6 | 138 ± 12 | 110 ± 6  | 95 ± 4   | 111 ± 5 | 91 ± 3 |
| 135 | 148 ± 7 | 140 ± 12 | 109 ± 6  | 98 ± 5   | 111 ± 3 | 91 ± 3 |
| 150 | 153 ± 4 | 141 ± 12 | 111 ± 5  | 100 ± 5  | 110 ± 3 | 95 ± 2 |
| 165 | 155 ± 5 | 138 ± 12 | 113 ± 6  | 103 ± 7  | 112 ± 4 | 99 ± 3 |
| 180 | 152 ± 5 | 141 ± 12 | 120 ± 8  | 101 ± 3  | 109 ± 5 | — |

Mean arterial blood pressure in conscious spontaneously hypertonic rats after oral administration of
Group 1: Placebo
Group 2: 0.1 mg/kg of chromakalim
Group 3: 0.3 mg/kg of chromakalim
Group 4: 1.0 mg/kg of chromakalim
Group 5: 0.1 mg/kg of chromakalim + 1.0 mg/kg of ramipril
Group 6: 0.3 mg/kg of chromakalim + 1.0 mg/kg of ramipril The combinations are prepared by either intensively mixing the individual components as powder or by dissolving the individual components in a suitable solvent such as, for example, a lower alcohol and then removing the solvent.

As mentioned above, the combinations according to the invention can be used in pharmaceuticals, particularly for the treatment of high blood pressure, cardiac insufficiency and coronary heart disease.

The combinations according to the invention can be administered orally or parenterally in an appropriate pharmaceutical preparation. For a form for oral administration, the active compounds are mixed with the additives customary therefor such as excipients, stabilizers or inert diluents and are brought by customary methods into suitable forms for administration, such as tablets, coated tablets, hard gelatin capsules, aqueous, alcoholic or oily suspensions or aqueous, alcoholic or oily solutions. Gum arabic, magnesium carbonate, potassium phosphate, lactose, glucose or starch, in particular maize starch, can, for example, be used as inert carriers. In this connection, the preparation can result both as dry or moist granules. Suitable oily excipients or solvents are, for example, vegetable and animal oils, such as sunflower oil or cod liver oil.

For subcutaneous or intravenous administration, the active compounds or their physiologically tolerable salts, if desired together with the substances customary for this such as solubilizers, emulsifiers or other auxiliaries, are brought into solution, suspension or emulsion. Possible solvents for the active combinations and the corresponding physiologically tolerable salts are, for example: water, physiological saline solutions or alcohols, for example ethanol, propanediol, or glycerol and in addition also sugar solutions such as glucose or mannitol solutions or a mixture of the different solvents mentioned.

Possible salts of the compounds of the formula I and II are, depending on the acidic or basic nature of these compounds, alkali or alkaline earth metal salts or salts with physiologically tolerable amines or salts with inorganic or organic acids such as, for example, HCl, HBr, $H_2SO_4$, maleic acid, fumaric acid, tartaric acid or citric acid.

The following example serves to illustrate the present invention without it being intended to limit it thereto:

EXAMPLE 1

Preparation of an oral combination preparation from ramipril and chromakalim 1000 tablets which contain 2 mg of ramipril and 0.3 mg of chromakalim are prepared as follows:

| | |
|---|---|
| ramipril | 2 g |
| chromakalim | 0.3 g |
| maize starch | 140 g |
| gelatin | 7.5 g |
| microcrystalline cellulose | 2.5 g |
| magnesium stearate | 2.5 g |

The two active compounds are mixed with an aqueous gelatin solution. The mixture is dried and ground to form granules. Microcrystalline cellulose and magnesium stearate are mixed with the granules. The granules prepared in this way are pressed to give 1,000 tablets, where each tablet contains 2 mg of ramipril and 0.3 mg of chromakalim.

We claim:
1. A pharmaceutical preparation containing
(a) an ACE inhibitor of the formula I

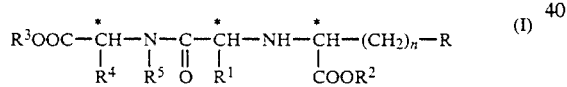

in which
n is 1 or 2,
R denotes hydrogen,
an optionally substituted aliphatic radical having 1-8 carbon atoms,
an optionally substituted alicyclic radical having 3-9 carbon atoms,
an optionally substituted aromatic radical having 6-12 carbon atoms,
an optionally substituted araliphatic radical having 7-14 carbon atoms,
an optionally substituted alicyclic-aliphatic radical having 7-14 carbon atoms,
a radical $OR^a$ or $SR^a$, in which
$R^a$ represents an optionally substituted aliphatic radical having 1-4 carbon atoms, an optionally substituted aromatic radical having 6-12 carbon atoms or an optionally substituted heteroaromatic radical having 5-12 ring atoms,
$R^1$ denotes hydrogen,
an optionally substituted aliphatic radical having 1-6 carbon atoms,
an optionally substituted alicyclic radical having 3-9 carbon atoms,
an optionally substituted alicyclic-aliphatic radical having 4-13 carbon atoms,
an optionally substituted aromatic radical having 6-12 carbon atoms,
an optionally substituted araliphatic radical having 7-16 carbon atoms,
an optionally substituted heteroaromatic radical having 5-12 ring atoms or
the side chain, protected if necessary, of a naturally occurring α-amino acid,
$R^2$ and $R^3$ are identical or different and denote hydrogen,
an optionally substituted aliphatic radical having 1-6 carbon atoms,
an optionally substituted alicyclic radical having 3-9 carbon atoms,
an optionally substituted aromatic radical having 6-12 carbon atoms,
an optionally substituted araliphatic radical having 7-16 carbon atoms and
$R^4$ and $R^5$ together with the atoms carrying them form a heterocyclic bi- or tricyclic ring system having 5 to 15 carbon atoms,
or its physiologically tolerable salt and
(b) a potassium channel modulator or its physiologically tolerable salt.

2. The preparation as claimed in claim 1, in which in the ACE inhibitor of the formula I
$R^4$ and $R^5$ together with the atoms carrying them form a ring system from the group comprising tetrahydroisoquinoline; decahydroisoquinoline; octahydroindole; octahydrocyclopenta[b]pyrrole; 2-azaspiro[4.5]decane; 2-azaspiro[4.4]nonane; spiro[-(bicyclo[2.2.1]heptane)-2,3'-pyrrolidine]; spiro[(bicyclo[2.2.2]octane)-2,3'-pyrrolidine]; 2-azatricyclo[4.3.0.$^{6.9}$]decane; decahydrocyclohepta[b]pyrrole; octahydroisoindole; octahydrocyclopenta[c]pyrrole; 2,3,3a,4,5,7a-hexahydroindole; 2-azabicyclo[3.1.0-]hexane; hexahydrocyclopenta[b]pyrrole, which can all be optionally substituted.

3. The preparation as claimed in claim 1, in which in the ACE inhibitor of the formula I
n is 1 or 2,
R denotes hydrogen,
alkyl having 1-8 carbon atoms,
alkenyl having 2-6 carbon atoms,
cycloalkyl having 3-9 carbon atoms,
aryl having 6-12 carbon atoms,
which can be monosubstituted, disubstituted or trisubstituted by ($C_1$-$C_4$)-alkyl, ($C_1$-$C_4$)-alkoxy, hydroxyl, halogen, nitro, amino, aminomethyl, ($C_1$-$C_4$)-alkylamino, di-($C_1$-$C_4$)-alkylamino, ($C_1$-$C_4$)-alkanoylamino, methylenedioxy, cyano and/or sulfamoyl,
alkoxy having 1-4 carbon atoms,
aryloxy having 6-12 carbon atoms,
which can be substituted as described above for aryl,
mono- or bicyclic heteroaryloxy having 5-7 or 8-10 ring atoms, of which 1 or 2 ring atoms are sulfur or oxygen atoms and/or 1 to 4 ring atoms are nitrogen,
which can be substituted as described above for aryl,
amino-($C_1$-$C_4$)-alkyl,
($C_1$-$C_4$)-alkanoylamino-($C_1$-$C_4$)-alkyl,
($C_7$-$C_{13}$)-aroylamino-($C_1$-$C_4$)-alkyl,
($C_1$-$C_4$)-alkoxycarbonylamino-($C_1$-$C_4$)-alkyl, ($C_6$–$C_{12}$)-aryl-($C_1$–$C_4$)-alkoxycarbonylamino-($C_1$–$C_4$)-alkyl,
($C_6$–$C_{12}$)-aryl-($C_1$–$C_4$)-alkylamino-($C_1$–$C_4$)-alkyl,
($C_1$–$C_4$)-alkylamino-($C_1$–$C_4$)-alkyl,
di-($C_1$–$C_4$)-alkylamino-($C_1$–$C_4$)-alkyl,
guanidino-($C_1$–$C_4$)-alkyl,
imidazolyl, indolyl,
($C_1$–$C_4$)-alkylthio,
($C_1$–$C_4$)-alkylthio-($C_1$–$C_4$)-alkyl,
($C_6$–$C_{12}$)-arylthio-($C_1$–$C_4$)-alkyl,
 which can be substituted in the aryl moiety as described above for aryl,
($C_6$–$C_{12}$)-aryl-($C_1$–$C_4$)-alkylthio,
 which can be substituted in the aryl moiety as described above for aryl,
carboxyl-($C_1$–$C_4$)-alkyl,
carboxyl, carbamoyl,
carbamoyl-($C_1$–$C_4$)-alkyl,
($C_1$–$C_4$)-alkoxycarbonyl-($C_1$–$C_4$)-alkyl,
($C_6$–$C_{12}$)-aryloxy-($C_1$–$C_4$)-alkyl,
 which can be substituted in the aryl moiety as described above for aryl or
($C_6$–$C_{12}$)-aryl-($C_1$–$C_4$)-alkoxy,
 which can be substituted in the aryl moiety as described above for aryl, $R^1$ denotes hydrogen,
alkyl having 1-6 carbon atoms,
alkenyl having 2-6 carbon atoms,
alkynyl having 2-6 carbon atoms,
cycloalkyl having 3-9 carbon atoms,
cycloalkenyl having 5-9 carbon atoms,
($C_3$–$C_9$)-cycloalkyl-($C_1$–$C_4$)-alkyl,
($C_5$–$C_9$)-cycloalkenyl-($C_1$–$C_4$)-alkyl,
aryl, which is optionally partly hydrogenated, having 6-12 carbon atoms, which can be substituted as described above for R,
($C_6$–$C_{12}$)-aryl-($C_1$–$C_4$)-alkyl or ($C_7$–$C_{13}$)-aroyl-($C_1$ or $C_2$)-alkyl
 which can both be substituted like the abovementioned aryl,
mono- or bicyclic heteroaryl, which is optionally partly hydrogenated, having 5-7 or 8-10 ring atoms, of which 1 or 2 ring atoms are sulfur or oxygen atoms and/or 1 to 4 ring atoms are nitrogen atoms,
 which can be substituted like the above-mentioned aryl or
the optionally protected side chain of a naturally occurring α-amino acid $R^1$—CH(NH$_2$)—COOH, $R^2$ and $R^3$ are identical or different and denote hydrogen, alkyl having 1-6 carbon atoms,
alkenyl having 2-6 carbon atoms,
di-($C_1$–$C_4$)-alkylamino-($C_1$–$C_4$)-alkyl,
($C_1$–$C_5$)-alkanoyloxy-($C_1$–$C_4$)-alkyl,
($C_1$–$C_6$)-alkoxycarbonyloxy-($C_1$–$C_4$)-alkyl,
($C_7$–$C_{13}$)-aroyloxy-($C_1$–$C_4$)-alkyl,
($C_6$–$C_{12}$)-aryloxycarbonyloxy-($C_1$–$C_4$)-alkyl, aryl having 6-12 carbon atoms,
($C_6$–$C_{12}$)-aryl-($C_1$–$C_4$)-alkyl,
($C_3$–$C_9$)-cycloalkyl or
($C_3$–$C_9$)-cycloalkyl-($C_1$–$C_4$)-alkyl and $R^4$ and $R^5$ have the meaning indicated in claim 1 or 2.

4. The preparation as claimed in claim 1, in which in the ACE inhibitor of the formula I
n is 1 or 2,
R denotes ($C_1$–$C_6$)-alkyl, ($C_2$–$C_6$)-alkenyl, ($C_3$–$C_9$)-cycloalkyl, amino-($C_1$–$C_4$)-alkyl, ($C_2$–$C_5$)-acylamino-($C_1$–$C_4$)-alkyl, ($C_7$–$C_{13}$)-aroylamino-($C_1$–$C_4$)-alkyl, ($C_1$–$C_4$)-alkoxycarbonylamino-($C_1$–$C_4$)-alkyl, ($C_6$–$C_{12}$)-aryl-($C_1$–$C_4$)-alkoxycarbonylamino-($C_1$–$C_4$)-alkyl, ($C_6$–$C_{12}$)-aryl which can be monosubstituted, disubstituted or trisubstituted by ($C_1$–$C_4$)-alkyl, ($C_1$–$C_4$)-alkoxy, hydroxyl, halogen, nitro, amino, ($C_1$–$C_4$)-alkylamino, di-($C_1$–$C_4$)-alkylamino and/or methylenedioxy, or 3-indolyl, in particular methyl, ethyl, cyclohexyl, tert.-butoxycarbonylamino-($C_1$–$C_4$)-alkyl, benzoyloxycarbonylamino-($C_1$–$C_4$)-alkyl or phenyl which can be monosubstituted or disubstituted by phenyl, ($C_1$–$C_2$)-alkyl, ($C_1$ or $C_2$)-alkoxy, hydroxyl, fluorine, chlorine, bromine, amino, ($C_1$–$C_4$)-alkylamino, di-($C_1$–$C_4$)-alkylamino, nitro and/or methylenedioxy or, in the case of methoxy, trisubstituted, $R^1$ denotes hydrogen or ($C_1$–$C_6$)-alkyl which can optionally be substituted by amino, ($C_1$–$C_6$)-acylamino or benzoylamino, ($C_2$–$C_6$)-alkenyl, ($C_3$–$C_9$)-cycloalkyl, ($C_5$–$C_9$)-cycloalkenyl, ($C_3$–$C_7$)-cyclcalkyl-($C_1$–$C_4$)-alkyl, ($C_6$–$C_{12}$)-aryl or partly hydrogenated aryl, which in each case can be substituted by ($C_1$–$C_4$)-alkyl, ($C_1$ or $C_2$)-alkoxy or halogen, ($C_6$–$C_{12}$)-aryl-($C_1$–$C_4$)-alkyl or ($C_7$–$C_{13}$)-aroyl-($C_1$–$C_2$)-alkyl, which can both be substituted in the aryl radical as defined in the foregoing, a mono- or bicyclic heterocyclic radical having 5 to 7 or 8 to 10 ring atoms, of which 1 or 2 ring atoms are sulfur or oxygen atoms and/or 1 to 4 ring atoms are nitrogen atoms, or a side chain of a naturally occurring, optionally protected α-amino acid, but in particular hydrogen, ($C_1$–$C_3$)-alkyl, ($C_2$ or $C_3$)-alkenyl, the optionally protected side chain of lysine, benzyl, 4-methoxybenzyl, 4-ethoxybenzyl, phenethyl, 4-aminobutyl or benzoylmethyl, $R^2$ and $R^3$ denote identical or different radicals hydrogen, ($C_1$–$C_6$)-alkyl, ($C_2$–$C_6$)-alkenyl or ($C_6$–$C_{12}$)-aryl-($C_1$–$C_4$)-alkyl, but in particular hydrogen, ($C_1$–$C_4$)-alkyl or benzyl and $R^4$ and $R^5$ have the meaning indicated in claim 1 or 2.

5. The preparation as claimed in claim 1, containing 2-[N-(1-S-ethoxycarbonyl-3-phenylpropyl)-S-alanyl]1S,3S,5S)-2-azabicyclo[3.3.0]octane-3-carboxylic acid or its physiologically tolerable salt.

6. The preparation as claimed in claim 1, containing 1-[N-(1-S-ethoxycarbonyl-3-phenylpropyl)-S-alanyl]-(2S,3aR,7aS)-octahydro[1H]indole-2-carboxylic acid or its physiologically tolerable salt.

7. The preparation as claimed in claim 1, containing 2-[N-(1-S-ethoxycarbonyl-3-phenylpropyl)-S-alanyl]-1,2,3,4-tetrahydroisoquinoline-3-S-carboxylic acid or its physiologically tolerable salt.

8. The preparation as claimed in claim 1, containing a potassium channel modulator of the formula II

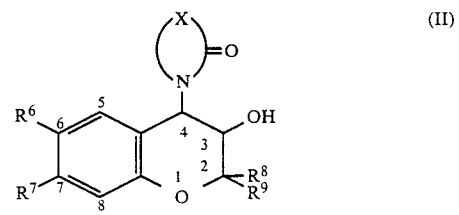

in which
$R^6$ represents CN, NO$_2$, SO$_n$—($C_1$–$C_6$)-alkyl or SO$_n$—Ar, where n is 1 or 2, Ar represents an aromatic or heteroaromatic system which is unsubstituted or substituted by 1 to 3 identical or different radicals from the series comprising ($C_1$–$C_2$)-alkyl, ($C_1$–$C_2$)-alkoxy, halogen, trifluoromethyl, CN, $NO_2$, CO-($C_1$–$C_2$)-alkyl or $SO_p$—($C_1$–$C_2$)-alkyl and p represents 1 or 2, $R^7$ represents hydrogen, hydroxyl, ($C_1$–$C_2$)-alkoxy, ($C_1$–$C_2$)-alkyl, halogen or $NR^{10}R^{11}$, where $R^{10}$ and $R^{11}$ are identical or different and represent hydrogen, ($C_1$–$C_2$)-alkyl or ($C_1$–$C_2$)-alkylcarbonyl, where the abovementioned meanings of $R^6$ and $R^7$ can also be interchanged, $R^8$ and $R^9$ are identical or different and represent alkyl having 1–4 carbon atoms, X represents a $(CH_2)_m$ chain which is unsubstituted or substituted by at least 1 and at rest $2m-1$ ($C_1$–$C_2$)-alkyl groups, and can be interrupted by a heteroatom Y with the meaning of O, $NR^{12}$ or S and $R^{12}$ denotes H or ($C_1$–$C_4$)-alkyl and m represents 2, 3 or 4, where the configuration of $C_3$ and $C_4$ is always opposite, or its physiologically tolerable salt.

9. The preparation as claimed in claim 1, containing a potassium channel modulator of the formula II in which X represents a $(CH_2)_m$ chain which is unsubstituted or substituted by a ($C_1$–$C_2$)-alkyl group, and can be interrupted by a heteroatom Y which represents O, S or $NR^{12}$ with $R^{12}$ having the meaning of hydrogen or ($C_2$–$C_4$)-alkyl, and where m represents 2, 3 or 4, or its physiologically tolerable salt.

10. The preparation as claimed in claim 1, containing a potassium channel modulator of the formula II in which X represents a $(CH_2)_m$ chain which is unsubstituted or substituted by a ($C_1$–$C_2$)-alkyl group where n represents 3 or 4, or its physiologically tolerable salt.

11. The preparation as claimed in claim 1, containing a potassium channel modulator of the formula II in which X represents a $(CH_2)_m$ chain, where m represents 3 or 4, which is substituted by a ($C_1$–$C_2$)-alkyl group on the carbon atom which is adjacent to the nitrogen atom of the lactam ring, or its physiologically tolerable salt.

12. The preparation as claimed in claim 1, containing a potassium channel modulator of the formula II in which X represents a $(CH_2)_m$ chain having m=3 or 4 which is unsubstituted or substituted by a ($C_1$–$C_2$)-alkyl group on the carbon atom which is adjacent to the nitrogen atom of the lactam ring, in particular in such a way that the configuration of this carbon atom is the same as that of the 4-carbon atom of the chroman system, or its physiologically tolerable salt.

13. The preparation as claimed in claims 1, containing a potassium channel modulator of the formula II in which $R^6$ represents $SO_2$—Ar with Ar having the meaning of phenyl which is unsubstituted or substituted by to 3 substituents as mentioned in clam 8, $R^7$ represents hydrogen or $OCH_3$, $R^8$ and $R^9$ are identical or different and represent ($C_1$–$C_2$)-alkyl, X represents a $(CH_2)_m$ chain having m=3 or 4 which is unsubstituted or substituted by a ($C_1$–$C_2$)-alkyl group on the carbon atom which is adjacent to the nitrogen atom of the lactam ring, in particular in such a way that the configuration of this carbon atom is the same as that of the 4-carbon atom in the chroman system, or its physiologically tolerable salt.

14. The preparation as claimed in claim 1, containing a potassium channel modulator of the formula II in which $R^6$ represents CN or $SO_2$—$CH_3$ and $R^7$ represents hydrogen, $R^8$ and $R^9$ are identical or different and represents alkyl having 1 to 2 carbon atoms, X represents a $(CH_2)_m$ chain having m=3 or 4 which is unsubstituted or substituted by a ($C_1$–$C_2$)-alkyl group on the carbon atom which is adjacent to the nitrogen atom of the lactam ring, in particular in such a way that the configuration of this carbon atom is opposite to that of the 4-carbon atom in the chroman system, or its physiologically tolerable salt.

15. The preparation as claimed in claim 1, containing ramipril+(±)-6-cyano-3,4-dihydro-2,2-dimethyl-trans-4-(2-oxo-1-pyrrolidinyl)-2H-benzo[b]pyran-3-ol (chromakalim) or, ramipril+6-cyano-3-hydroxy-2,2-dimethyl-4-(5-methyl-2-oxo-1-pyrrolidinyl)-3,4-dihydro-2H-benzo[b]pyran or ramipril+2,2-dimethyl-3-hydroxy-6-phenylsulfonyl-4-(2-oxo-1-pyrrolidinyl)-3,4-dihydro-2H-benzo[b]pyran or trandolapril+chromakalim or trandolapril+6-cyano-3-hydroxy-2,2-dimethyl-4-(5-methyl-2-oxo-1-pyrrolidinyl)-3,4-dihydro-2-H-benzo[b]pyran or trandolapril+2,2-dimethyl-3-hydroxy-6-phenylsulfonyl-4-(2-oxo-1-pyrrolidinyl)-3,4-dihydro-2H-benzo[b]pyran or quinapril+chromakalim or quinapril+6-cyano-3-hydroxy-2,2-dimethyl-4-(5-methyl-2-oxo-1-pyrrclidinyl)-3,4-dihydro-2H-benzo[b]pyran or quinapril+2,2-dimethyl-3-hydroxy-6-phenylsulfonyl-4-(2-oxo-1-pyrrolidinyl)-3,4-dihydro-2H-benzo[b]pyran or ramipril+(3S,4R)-6-cyano-3,4-dihydro-2,2-dimethyl-4-(2-oxo-1-pyrrolidinyl)-2H-benzo[b]pyran-3-ol or, trandolapril+(3S,4R)-6-cyano-3,4-dihydro-2,2-dimethyl-4-(2-oxo-1-pyrrolidinyl)-2H-benzo[b]pyran-3-ol or quinapril+(3S,4R)-6-cyano-3,4-dihydro-2,2-dimethyl-4-(2-oxo-1-pyrrolidinyl)-2H-benzo[b]pyran-3-ol or ramipril+(3S,4R)-6-phenylsulfonyl-3,4-dihydro-2,2-dimethyl-4-(2-oxo-1-pyrrolidinyl)-2H-benzo[b]pyran-3-ol or trandolapril+(3S,4R)-6-phenylsulfonyl-3,4-dihydro-2,2-dimethyl-4-(2-oxo-1-pyrrolidinyl)-2H-benzo[b]pyran-3-ol or quinapril+(3S,4R)-6-phenylsulfonyl-3,4-dihydro-2,2-dimethyl-4-(2 oxo-1-pyrrolidinyl)-2H-benzo[b]pyran-3-ol and in each case the physiologically tolerable salts of the individual components mentioned, if these can be formed.

16. The use of a preparation as claimed in claim 1 in the treatment of high blood pressure, cardiac insufficiency and/or coronary heart disease.

17. A product containing (a) an ACE inhibitor of the formula I or its physiologically tolerable salt and (b) a potassium channel modulator of the formula II or its physiologically tolerable salt as a combination preparation for simultaneous, separate or sequential administration in the treatment of high blood pressure.

* * * * *

UNITED STATES PATENT AND TRADEMARK OFFICE
CERTIFICATE OF CORRECTION

PATENT NO. : 4,975,453
DATED : December 04, 1990
INVENTOR(S) : Reinhard Becker et al.

It is certified that error appears in the above-identified patent and that said Letters Patent is hereby corrected as shown below:

Claim 2, column 12, line 36, change "$[4.3.0^{6.9}]$ to $--[4.3.0.1^{6,9}]--$

Claim 4, column 14, line 19, change "cyclcalkyl" to --cycloalkyl--

Claim 5, column 14, line 42, change "]1S" to --]-(1S --

Claim 8, column 15, line 14, change "rest" to --most --

Claim 10, column 15, line 32, change "m" to --⏋--.

Claim 13, column 15, line 57, insert --1-- after "by"

Claim 13, column 15, line 58, change "clam" to --claim--

UNITED STATES PATENT AND TRADEMARK OFFICE
CERTIFICATE OF CORRECTION

PATENT NO.  : 4,975,453
DATED       : December 04, 1990
INVENTOR(S) : Reingard Becker et al.

It is certified that error appears in the above-identified patent and that said Letters Patent is hereby corrected as shown below:

Claim 14, column 16, line 6, change "represents" to --represent--

Claim 15, column 16, line 27, change "2-H" to --2H--

Claim 15, column 16, line 34, change "pyrrclidinyl" to --pyrrolidinyl--

Claim 15, column 16, line 52, change "2 oxo" to --2-oxo--

Signed and Sealed this

Twelfth Day of January, 1993

Attest:

DOUGLAS B. COMER

*Attesting Officer*  *Acting Commissioner of Patents and Trademarks*